United States Patent [19]

Samuelson et al.

[11] 4,232,404
[45] Nov. 11, 1980

[54] ENDOPROSTHETIC ANKLE JOINT

[75] Inventors: Kent M. Samuelson, Salt Lake City, Utah; Michael A. Tuke, Morden, England

[73] Assignee: National Research Development Corporation, London, England

[21] Appl. No.: 923,687

[22] Filed: Jul. 11, 1978

[30] Foreign Application Priority Data

Jul. 18, 1977 [GB] United Kingdom ............... 30073/77

[51] Int. Cl.³ ............................................. A61F 1/03
[52] U.S. Cl. ..................................... 3/1.91; 128/92 C
[58] Field of Search ................... 3/1.91, 1.9; 128/92 C

[56] References Cited

U.S. PATENT DOCUMENTS

| 3,839,742 | 10/1974 | Link | 3/1.91 |
|---|---|---|---|
| 3,879,767 | 4/1975 | Stubstad | 3/1.91 |
| 3,889,300 | 6/1975 | Smith | 3/1.91 |
| 3,896,502 | 7/1975 | Lennox | 3/1.91 |
| 3,896,503 | 7/1975 | Reykers et al. | 3/1.91 |
| 3,975,778 | 8/1976 | Newton | 128/92 C X |
| 3,987,500 | 10/1976 | Schlein | 3/1.91 |
| 4,021,864 | 5/1977 | Waugh | 3/1.91 |
| 4,069,518 | 1/1978 | Groth, Jr. et al. | 3/1.91 |

OTHER PUBLICATIONS

Lord, et al., *Revue de Chirurgie Orthopedigue;* "Prosthesis Totale de Cheville", 1973, 59, pp. 140–141.
Smith, *Smith Total Ankle Surgical Procedure,* 1973, 1 page.
Scholz, *A Total Ankle Replacement Prosthesis,* Date Unknown, 1 page.

*Primary Examiner*—Clifford D. Crowder
*Attorney, Agent, or Firm*—Cushman, Darby & Cushman

[57] ABSTRACT

An endoprosthetic ankle joint device comprises a talar component with a convex articulatory surface having an intermediate part-circular-cylindrical area coaxially flanked at each end by like mutually divergent part-conical areas, and a tibial component with an assymetrical concave articulatory surface complementary with said convex cylindrical area and one of said conical areas. In one form of the device the tibial concave surface has areas complementary with each of the talar conical areas, but to different extents, with the former areas being respectively axially longer and shorter. In another form, the tibial concave surface is only complementary with one of the talar conical areas, and the device comprises a fibular component for articulation with the other talar conical area.

4 Claims, 7 Drawing Figures

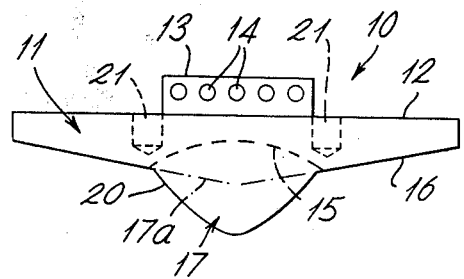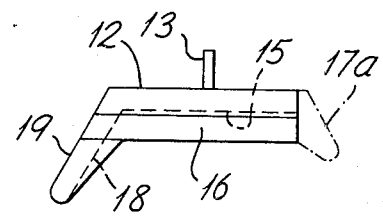
Fig. 1     Fig. 2
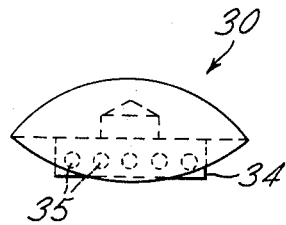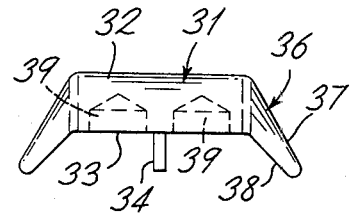
Fig. 3     Fig. 4
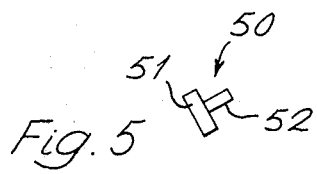
Fig. 5
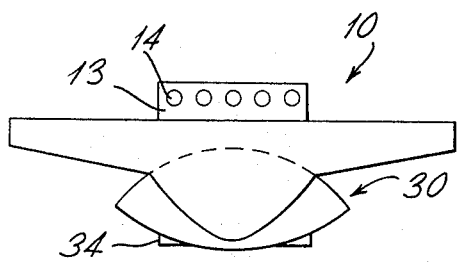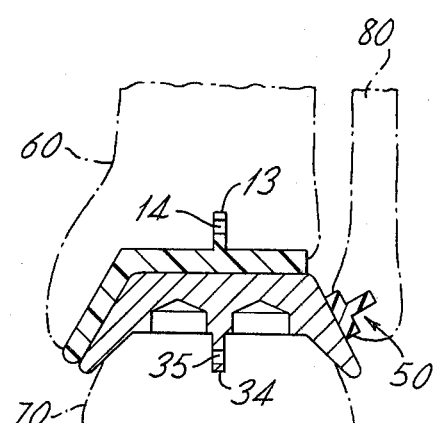
Fig. 6     Fig. 7

ENDOPROSTHETIC ANKLE JOINT

This invention concerns endoprosthetic bone joint devices and more particularly such devices for use in an ankle joint prosthesis.

Previous proposals for endoprosthetic ankle joint devices have mostly employed one or other of two forms. One form comprises a tibial component defining a concave surface of revolution of open-ended part-cylindrical or barrel form, the talar component defining a convex surface of revolution substantially complementary to said concave surface for mutual articulatory bearing engagement therewith, and these components being adapted remotely from said surfaces for respective securement to the tibia and talus. The other form of device is essentially similar, but the tibial component has wall portions closing the ends of its concave surface. Examples of devices of these forms are described in U.K. Pat. Nos. 1,447,368 and 1,446,593.

However embodiments of these forms of device so far used in clinical practice do not appear to be wholly satisfactory because there is a risk of continuing pain. This risk is thought to arise with direct engagement of bone with bone.

An object of the present invention is to provide an improved endoprosthetic ankle joint device which obviates the risk of engagement as just discussed, and such a device comprises a talar component defining a convex articulatory surface of revolution of which the generator has an intermediate portion and two end portions extending in mutually divergent manner from respectively opposite ends of said intermediate portion, and a tibial component defining an assymetrical concave articulatory surface of rotation substantially complementary with part of said convex surface as generated by said intermediate portion and one of said end portions, said components being adapted remotely from said surfaces for respective securement to the talus and tibia.

It will be appreciated that this device differs from the earlier forms mentioned above by extending the articulatory surface of the talar component so that it includes end portions relative to the axis of rotation, and it will be seen below that these end portions articulate with co-operating component portions whereby the surfaces of the different bones in the joint are maintained out of contact with each other and with relatively movable components.

In practice two forms of device are appropriate for this purpose.

In one form, the tibial component has its articulatory surface complementary only with the intermediate portion and one end portion of that of the talar component, and the former surface is located in substitution for the inferior and the medial malleolar areas of the natural tibial articular surfaces. Since one end portion of the talar articulatory surface is then otherwise exposed to possible engagement with the fibular malleolus, an additional component is provided for securement in the fibula to act as a buffer which itself engages and articulates with the talar component. This form of device is only readily suited to use in a situation where the fibular malleolus is sufficiently sound that securement of the relevant component thereto presents no difficulty, bearing in mind the relatively small extent of the available securement site.

The other form of the present device caters for the situation where the last-mentioned securement is not readily practicable. In this instance the tibial articulatory surface has portions complementary with each of the portions of the talar articulatory surface, but the end portions of the former surface are respectively deeper and shallower. In practice, the shallower end portion is located adjacent to the fibula, and the articular surface of the fibular malleolus is resected to avoid engagement therewith.

In both forms of the proposed device it is preferred that the intermediate and end portions of the articulatory surfaces of revolution be defined by corresponding generator portions which are rectilinear with the intermediate portion parallel to, and the end portions equally but oppositely inclined to, the axis of rotation. In the result this provides surfaces with part-cylindrical intermediate portions flanked at at least one end by a part-conical portion. Such surface shapes conform reasonably well with the shapes of the natural talar and tibial articular surfaces and it is therefore possible, given appropriate dimensioning of the components, for the components to blend correspondingly well as far as exterior shape is concerned with the bones in which they are secured.

In this last respect it is also preferred that an additional measure be taken with the tibial component. This measure involves the provision of such a component comprising a body of plastics material of elongated slab form having the intermediate portion of the relevant concave articulatory surface formed longitudinally across the width of a central portion of the slab. The slab accordingly provides flanges extending from the longitudinal perpheries of the concave surface and, by making the tibial component of a suitable plastics material and by making the slab longer than the maximum likely size of the corresponding tibial dimension, the flanges overhang the tibial site and can be cut to conform therewith during the operative procedure.

A fuller understanding of the present invention and preferred forms thereof will be gathered from the following description thereof, given by way of example, with reference to the accompanying drawings, in which:

FIGS. 1 and 2 diagrammatically illustrate a tibial component of one embodiment of the invention in side and end elevations, respectively, FIGS. 3 and 4 similarly illustrate the associated talar component, FIG. 5 illustrates an associated fibular malleolar component, and FIGS. 6 and 7 schematically illustrate the components of FIGS. 1 to 5 in articulatory engagement in respective side elevation and transverse cross-sectional views.

The illustrated tibial component is denoted generally at 10 and comprises a main body portion 11 in the form of an elongated slab which is generally rectangular in plan view. One major face 12 of the body portion 11 is planar and has a rib 13 extending from a central longitudinal part thereof, the rib being transversely bored to provide a sequence of apertures 14 therethrough. Also, the body portion 11 is partially transversely bored therethrough from the face 12 to provide two holes 21 respectively located adjacent the ends of the rib 13. The other major face of the body portion 11 has its central longitudinal part dished to define a concave part-circular-cylindrical surface 15 extending thereacross, and the remaining parts of this face are each in the form of a planar surface 16 which convergently inclines relative to the face 12 towards their corresponding longitudinal free ends.

The remaining part of the tibial component comprises a transverse body portion 17 which projects from the main body portion 11 adjacent one longitudinal end of the cylindrical surface 15. The body portion 17 projects into the cylindrical space defined by completion and elongation of the surface 15 and, more specifically, inclines outwardly from the cylindrical space actually bounded by the surface 15. The inner face of the portion 17 facing towards the last-mentioned space defines a concave part-conical surface 18 coaxial with the surface 15, the outer face of the portion 17 is a planar surface 19, and the free edge 20 of the portion 17 defines a convex curve discussed below relative to the talar component.

The tibial component as so far described can be of a modified form having a further transverse body portion projecting from the other side of the main body portion. This further portion will be a reflected version of portion 17, but not project as far, and is denoted in broken line 17a in FIG. 2. The free edge of portion 17a follows the lines of the planar surfaces 16 when projected towards each other. Both this and the original form of component are symmetrical about their transverse medial planes to allow use in the left or right tibia. Also both forms are of one-piece construction from plastics material such as ultra high molecular weight polyethylene.

The illustrated talar component is denoted generally as 30 and comprises a main body portion 31 of which the two major faces respectively define a convex part-circular cylindrical surface 32 and a planar surface 33. The cylindrical surface 32 is complementary to and of equal longitudinal extent to the surface 15 of the tibial component, but the surface 32 is of greater circumferential extent than surface 15. The planar surface 33 has a rib 34 extending therefrom, the rib having apertures 35 similarly to the rib 13 of the tibial component, and the rib 34 being located in the medial transverse radial plane relative to surface 32. Also, the body portion 31 is partially transversely bored therethrough from the surface 33 to provide two holes 39 respectively located on opposite sides of the rib 34.

The remaining parts of the talar component comprise two transverse body portions 36 which project from the main body portion 31 respectively adjacent the longitudinal ends of the cylindrical surface 32. The portions 36 extend towards the axis of surface 32 in mutually divergent manner. Each portion 36 has an outer major face defining a part-conical surface 37 coaxial with the cylindrical surface 32 and complementary with the part-conical surface 18 of the tibial component, each portion 36 has a planar inner surface 38, and each portion 36 has a circular arcuate free edge. One of the surfaces 37 articulates coaxially with the surface 18, as will be apparent from FIGS. 6 and 7 described hereinafter, and the limiting positions of this articulation when simulating normal ankle joint movement are employed to determine the free edge curved shape of the transverse body portion 17 of the tibial component. This shape is seen to comprise two like halves which are mutual reflections and each such half is substantially the same as a corresponding half of the free edge curve of talar component portion 36 when at the innermost position of its simulating range of articulation. In the result, the free edges of the portion 36 do not articulate across the surface 18.

The talar component 30 is symmetrical both about its longitudinal and transverse medial radial planes. Also the component is of one-piece construction from metal such as chrome-cobalt-alloy.

The illustrated fibular malleolar component is of simple stemmed stud form. The component is denoted generally as 50, it has a head 51 of rectangular disc form from one of the major faces of which a stem 52 projects. Also the component is of one-piece construction from the same material as the tibial component.

Use of the illustrated components is indicated by FIGS. 6 and 7 in which the components are shown in mutually articulatory engaged positions, with FIG. 7 additionally showing adjacent portions of the tibia, talus and fibula at 60, 70 and 80, respectively, in chain line. It will be seen that, after suitable surgical exposure of the joint and preparation of the bone sites, the components are located to substitute their articulatory surfaces for the natural articular surfaces. More specifically, the talar component is located on the talus with the articulatory surfaces of the former aligned for rotation in the sagittal plane of the latter, the tibial component is correspondingly located with its part-cylindrical and part-conical surfaces substituted for the distal and malleolar articular surfaces of the tibia, and the fibular malleolar component is located so that its free major face replaces the role of the natural articular surface of the fibula and engages the explosed part-conical surface of the talar component. In the case where the modified tibial component is employed, the further transverse body portion engages the talar component in place of the fibular malleolar component and the articular surface of the fibular malleolus is resected to avoid the possibility of contact with either of the remaining components.

These locations are to be secured by the use of bone cement in generally conventional manner, keyed in the holes 21 and 39, although it is preferred that the cement should not be applied over the apertured ribs of the talar and tibial components. These ribs are designed to allow bone in-growth into their apertures.

Before final securement the longitudinal end portions of the tibial component involving surfaces 16 can be trimmed to conform to the shape of the adjacent tibial bone.

While the present invention has been described with more detailed reference to the illustrated embodiments, it will be understood that variations are possible within the broader proposal discussed in the introductory passages hereinbefore. Such variations can involve the specific geometry of the articulatory surfaces of the components, their adaption for the purposes of securement, and the choice of materials.

We claim:
1. An endoprosthetic ankle joint device, comprising:
a talar component defining, relative to an axis, a convex articulatory surface of revolution of which the generator has a rectilinear intermediate portion parallel to said axis and two rectilinear end portions extending in equally inclined divergent manner towards said axis, so that said convex surface is formed by a part-circular-cylindrical area flanked at each end by a coaxial part-conical area;
a tibial component defining, relative to said axis, an assymmetrical concave surface of revolution substantially complementary with and in articulatory engagement with said cylindrical area and only one of said conical areas; and a fibular component having an articulatory surface engaged with the other of said conical areas;

said components being adapted remotely from said surfaces for respective securement to the talus, tibia, and fibula;

said talar component being, as a whole, symmetrical about the medial axial radial plane and the medial transverse radial plane of said cylindrical area; and said tibial component being, as a whole, symmetrical about said axial plane.

2. A device according to claim 1 wherein said fibular component articulatory surface is planar.

3. An endoprosthetic ankle joint device, comprising:

a talar component defining, relative to an axis, a convex articulatory surface of revolution of which the generator has a rectilinear intermediate portion parallel to said axis and two rectilinear end portions extending in equally inclined divergent manner towards said axis, so that said convex surface is formed by a part-circular-cylindrical area flanked at each end by a coaxial part-conical area; and a tibial component defining, relative to said axis, a concave surface of revolution formed by areas substantially complementary with and in articulatory engagement with said cylindrical and conical areas, said concave surface being assymmetrical by having its two areas complementary to said conical areas of greater and lesser axial extent;

said components being adapted remotely from said surfaces for respective securement to the talus and tibia;

said talar component being, as a whole, symmetrical about the medial axial radial plane and the medial transverse radial plane; and said tibial component being, as a whole, symmetrical about said axial plane.

4. An endoprosthetic ankle joint, comprising:

a talar component defining, relative to an axis, a convex articulatory surface of revolution of which the generator has a rectilinear intermediate portion parallel to said axis and two rectilinear end portions extending in equally inclined divergent manner towards said axis, so that said convex surface is formed by a coaxial part-circular-cylindrical area flanked at each end by a coaxial part-conical area; and a tibial component defining, relative to said axis, an assymmetrical concave surface of revolution substantially complementary with and in articulatory engagement with part of said convex surface as generated by said intermediate portion and one of said end portions;

said components adapted remotely from said surfaces for respective securement to the talus and tibia;

said components being respectively made of relatively harder and softer materials;

said concave surface being of a lesser angle of revolution than said convex surface;

said convex conical areas having substantially circular arcuate free edges and the complementary area of said concave surface having a free edge having halves of like, but mutually reflected, substantially circular arcuate shape to colinearly overlie the corresponding halves of the respective adjacent circular arcuate free edges of said convex conical areas at respective limits of a predetermined range of articular movement between said components;

said tibial component being made from a single body of said softer material, which material is trimmable by cutting during an operative procedure utilizing said device, and said body having a main part of generally slab form in a longitudinally central part of which the area of said concave surface complementary to said convex cylindrical area is defined axially transversely thereacross;

said talar component being, as a whole, symmetrical about the medial axial radial plane and the medial transverse radial plane of said convex cylindrical area; and said tibial component being substantially symmetrical as a whole about medial planes passing therethrough.

* * * * *